United States Patent [19]
Brandman et al.

[11] 3,932,654

[45] Jan. 13, 1976

[54] PRESERVATION OF AQUEOUS SYSTEMS WITH DIALKYL BROMONITROMALONATES

[75] Inventors: Harold A. Brandman, Glen Ridge; Milton Manowitz, Fair Lawn; William E. Newman, Montclair, all of N.J.

[73] Assignee: Givaudan Corporation, Clifton, N.J.

[22] Filed: May 22, 1974

[21] Appl. No.: 472,397

Related U.S. Application Data

[63] Continuation of Ser. No. 209,988, Dec. 20, 1971, abandoned.

[52] U.S. Cl. ............... 424/313; 162/161; 252/49.5; 252/403; 260/45.85; 71/67
[51] Int. Cl.² ........................................ A01N 9/24

[58] Field of Search ................................... 424/313

[56] References Cited
UNITED STATES PATENTS

| | | | |
|---|---|---|---|
| 2,651,590 | 9/1953 | Karsten | 424/313 |
| 3,098,039 | 7/1963 | Hodge | 424/313 |

OTHER PUBLICATIONS

Chemical Abstracts, Vol. 57 (1962), p. 5842f.

*Primary Examiner*—V. D. Turner
*Attorney, Agent, or Firm*—Thomas Cifelli, Jr.

[57] ABSTRACT

The present invention relates to processes and compositions for inhibiting or preventing the growth of microorganisms in aqueous systems and formulations, by the addition thereto of dialkyl bromonitromalonates.

6 Claims, No Drawings

PRESERVATION OF AQUEOUS SYSTEMS WITH DIALKYL BROMONITROMALONATES

This application is a continuation of application Ser. No. 209,988 filed Dec. 20, 1971, now abandoned.

DESCRIPTION OF THE PRIOR ART

The control of microbial growth in aqueous systems and products is a formidable problem. It is a matter of record that the water systems in a large variety of industries are susceptible to the formation of slime due to these microorganisms resulting in expensive delays and equipment repairs. It is also well known that very many industrial and consumer products and formulations that contain water can be damaged or completely destroyed by the growth of bacteria, fungi, and algae. Examples of such systems and compositions are industrial cooling water, water used in pulp and paper manufacture ("white water"), flood water used in secondary oil recovery, cosmetic products (lotions, emulsions, etc.), liquid soaps and detergents, textile emulsions, cutting oils, polymer emulsions, latex paints, adhesives, emulsion waxes and rolling mill lubricants.

Many useful preservatives have been proposed for these systems and products, but very often have proved to be unsatisfactory due to rapid loss of activity, inactivation by components of the system, incompatibility, toxicity, etc.

For example, the presence of oil or nonionic surfactants in these systems will inactivate a large number of biocides. In many instances, known antimicrobial agents are effective only against certain groups of microorganisms and will fail to protect systems that are contaminated with other types of microflora. For example, many biocides are active against gram-positive bacteria and fungi but show feeble or no activity against gramnegative organisms such as the Pseudomonas species that are ubiquitous spoilage organisms. The increasing demands of higher environmental health and pollution control standards have also imposed significant limitations on the use of many known antimicrobial agents such as mercurials and chlorinated phenols.

Cutting oil emulsions are widely used in the high speed metal cutting industries for their cooling, lubricating and anticorrosive properties. These systems are very susceptible to bacterial decomposition producing obnoxious odors and potential hazards unless adequately protected by the addition of an effective preservative.

A cutting oil emulsion consists of 1% to 20% of an emulsifiable cutting oil in water. Emulsifiable cutting oils are composed of petroleum oils mixed with emulsifying agents; usually a soap of petroleum sulfonate, fatty acid, tall oil, or resin.

Detailed descriptions of these systems their microbiological problems and difficulties in their preservation can be found in: Bennet, E. O., Soap Chem. Specialties, 32, 46 (1956), and Fabian, F. W. and Pivnick, H., Applied Microbiology, 1, 201 (1953).

Cosmetic products formulated with water are very susceptible to the growth of microorganisms. Complete descriptions and formulations of cosmetic products are well known to those skilled in the art and are found in Sagarin, E., *Cosmetic-Science and Technology*, Interscience Publishers, Inc., New York (1957).

Microbial contamination of cosmetics represent not only a spoilage problems but also a public health menace to the consumer. Problems encountered in the preservation of these materials are described by Dunnigan, A. P., Drug and Cosmetic Industries, 102, 43, (1968).

Microbial growth in papermill water systems presents a major problem to that industry. The application of effective antimicrobials to these systems, often called white water systems, is necessary to avoid the problems and economic losses due to the microorganisms. Papermill water systems normally contain up to 15% of cellulosic fiber material and present favorable conditions for microbial growth. A detailed description of these systems is presented in U.S. Pat. No. 3,397,144.

Cooling towers are widely used in industry for cooling and recirculating large quantities of water used in heat exchange operations. The problems of microbial growth in these systems causing slime formations which markedly impair the efficiency is well known and is described in *Betz Handbook of Industrial Water Conditioning*, Betz Laboratories, Inc., Philadelphia, Pa.

The growth of microorganisms, especially the anaerobe, *Desulfovibrio desulfuricans*, in flood waters used in secondary oil recovery presents serious problems to the petroleum industry. These problems are discussed in Meyers and Slabgi, "The Microbiological Quality of Injection Water used in Alberta Oil Fields", Producers Monthly, 12, May (1962). The addition of antimicrobial compounds which are active at very low concentrations provides a satisfactory solution to this problem. A recommended procedure for determining the effectiveness of a chemical in this application is to test the activity of the chemical against selected bacteria. (See API Recommended Practice for Biological Analysis of Subsurface Injection Water, American Petroleum Industries, New York).

Emulsion paints, often termed latex or water based paints are subject to microbial deterioration during storage. An adequate description of these paints is found in the Rohm and Haas Company's brochure "Rhoplex Acrylic Emulsions for Outdoor Paints", 11th Annual Progress Report. The in-can spoilage of emulsion paints is most frequently attributed to the growth of gram negative bacteria which can produce noxious odors, gas formation, discoloration, and complete destruction of the emulsion.

The problems resulting from microbial contamination of rolling mill oils and emulsions were reviewed by E. C. Hill in Metals and Materials, p. 294–297, September, 1967.

Lubricants or "spin finishes", that are applied to synthetic and natural fibers to facilitate processing are composed of various organic ingredients diluted with water. These lubricants are susceptible to microbial attack leading to the formation of noxious odors, discoloration and emulsion breakdown.

Polymer emulsions generally provide an excellent environment for the growth of microorganisms. These emulsions are used for the preparation of a variety of products including paints, paper coatings, floor coatings, and printing inks. Polymer emulsions are aqueous emulsions of thermoplastics usually containing about 50% solids. In addition to the polymers such as styrenebutadiene, acrylics, polyvinyl acetate, and polyvinyl copolymers, these emulsions also may contain surfactants, release agents, lubricants and plasticizers.

Adhesives, particularly starch base adhesives, usually do not contain preservatives, however, these unpreserved adhesives are sensitive to microbial degradation and spoilage.

SUMMARY OF THE INVENTION

We have discovered a class of antimicrobial compounds that, when added to the aqueous systems and compositions described above, effectively prevent the growth of damaging bacteria, fungi, and algae. Furthermore, it was found that this group of compounds is much more effective against the spoilage organisms than known antimicrobial agents and thus will protect these systems at much lower concentrations than the known agents.

The antimicrobial agents of this invention are esters of bromonitromalonic acid and may be represented by the following structural formula:

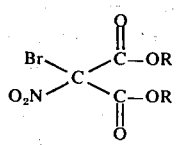

wherein R is a member selected from the group consisting of straight or branched chain alkyl having up to 4 carbon atoms.

Although some of the active compounds of this invention are not novel compounds, their potent antimicrobial properties and their utility as effective antimicrobial preservatives in various aqueous systems and compositions has not been disclosed or rendered obvious in the literature.

The active compounds of this invention were prepared by nitrating and then brominating the corresponding malonic acid esters. Optionally, some of the higher molecular weight esters may be prepared by transesterification of dimethyl or diethyl bromonitromalonate with the higher alcohols. The general method of preparation is illustrated by the following reaction scheme.

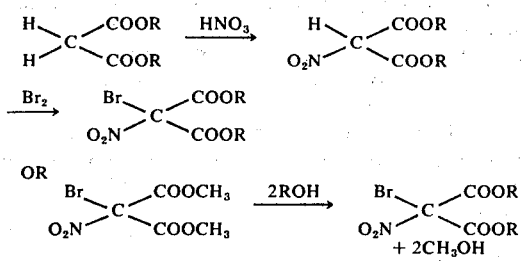

DESCRIPTION OF THE PREFERRED EMBODIMENTS

The compounds are active both in acid and basic media and are not inactivated by the presence of nonionic surfactants or large quantities of fats, oils, resins, etc.

The compounds may be added to the aqueous systems or formulations undiluted or dissolved in organic solvents such as alcohols, acetone, dimethylformamide, benzene, p-dioxane, carbon tetrachloride and various other industrual solvents. Incorporation of the compounds may be made at any step during the preparation of the formulated products. For example, in the case of oil in water systems or formulations, the chemicals may be initially added to the oil phase prior to formulation of the final product or by adding them to the completed system or formulation.

The compounds may be added to the aqueous systems and formulations alone or in combination with other biocides and/or functional compounds such as antioxidants, anticorrosive agents, surfactants, etc.

The active compounds of this invention, in general, are effective against a broad spectrum of microorganisms which attack aqueous systems and formulations. Examples of some of these microorganisms are:

Gram Positive Bacteria

*Staphylococcus aureus*
*Staphylococcus epidermidis*
*Bacillus subtilis*

Gram Negative Bacteria

*Escherichia coli*
*Pseudomonas aeruginosa*
*Proteus vulgaris*
*Pesudomonas fluoroescens*
*Aerobacter aerogenes*
*Salmonella typhosa*
*Salmonella cholerasuis*

Yeasts

*Candida albicans*

Molds

*Penicillium piscarium*
*Aspergillus niger*
*Aspergillus oryzae*
*Aureobasidium pullulans*

Small quantities of our compounds are sufficient to prevent microbial growth in the aqueous systems and formulations. Concentrations as low as 0.0001% to 0.1% by weight have given effective results. The use of greater quantities, while feasible, is recommended only for unusual applications. Concentrations of between 0.005% and 0.05% are preferred.

The compounds of the present invention may be utilized as preservatives for cutting oil emulsions. Solutions of the active compounds in a suitable solvent such as dimethylformamide or ethanol, having a strength of between about 5 to about 10% by weight, prepared, and added to the cutting oil in order to give a concentration of between about 100 to about 30 parts of cutting oil per part of active compound.

The compounds of our invention are found to be very effective preservatives for cosmetic compositions and are especially advantageous in formulations containing nonionic surfactants that are known to nullify the antimicrobial properties of a great many known preservatives. The compounds may be added to the finished cosmetic product directly or dissolved in suitable solvents such as alcohol, acetone, dimethylformamide, etc. Alternately the compounds may be dissolved in the oils or other raw materials used in the formula and then formulated into the final product.

The compounds may also be used to protect the so-called white water systems utilized in paper manufacture from the formation of slimes and the like which are known to affect these systems. Concentrations of the order of from about 30 to about 250 mcg of active compounds per ml. of white water are effective.

Concentrations of between 25 to 50 mcg of active compounds per ml. of water are effective in decreasing the aerobic bacterial count from water used in cooling tower water systems.

Flood waters used in the secondary recovery of oil in oil wells are particularly susceptible to attack by D. desulfuricans. Protection against this microorganism may be obtained utilizing between about 50 to about 100 mcg of active compound per ml. of flood water. Water base emulsion paints, such as acrylic emulsion house paint may be protected against microbial spoiling by the addition thereto from about 60 to about 125 mcg of the active compound per ml. of paint.

Similarly, rolling mill oils and emulsiions without water base, may be protected against microbial degradation by the addition thereto of alkanolic, preferably ethanolic solutions of the active compounds to yield a concentration from about 30 to about 60 mcg/ml. of emulsions.

The textile lubricants such as spin finishes may also be protected by the addition of ethanolic solutions of the active compound of the present invention. The protected composition contains between about 20 to about 125 mcg of the active compound per ml. of the lubricant.

Adhesives, particularly starch base adhesives, may be protected by adding thereto from about 20 to about 250 mcg of the active compounds per ml. of adhesive.

The compounds of the present invention may be prepared by methods well known in the art. In the preferred procedure which may be used for the preparation of all of the compounds of the present invention, but which is preferably used for the synthesis of diethyl or dimethyl bromonitromalonate, the dialkylmalonate is treated with concentrated nitric acid at ambient temperatures. The mixture is maintained at this temperature from about 1 to about 4 hours, quenched by pouring into ice water, and extracted with a suitable water immiscible solvent such as benzene, toluene, or the like. The organic extract is then washed to neutrality with a mild base suitably sodium bicarbonate and worked up in the usual manner. Upon removal of the solvent, the residue is distilled under reduced pressure to yield the desired dialkylnitromalonate.

To a solution of the dialkylnitromalonate in a lower alkanol, suitably the alkanol corresponding to the alkyl group, is added a solution of an alkali metal alkylate, suitably the sodium alkylate of the alkanol used. There is added to this solution a slight excess of bromine, and the reaction mixture quenched by the addition of saturated aqueous sodium chloride. The aqueous mixture is extracted with a water immiscible solvent, suitably ether, which is then worked up in the usual manner to yield a residue which, upon distillation of the reduced pressure, yields the desired dialkyl bromonitromalonate.

If desired, higher dialkyl bromonitromalonates may be prepared by transesterification of dimethyl or diethyl bromonitromalonate with higher alkanols in the usual manner.

EXAMPLE I

Concentrated nitric acid (184 ml.) was added slowly to 80 g. of diethyl malonate at 15°–20° and agitated an additional 3 hours at this temperature range. The nitrated ester was poured into one liter of ice water and then extracted twice with 200 ml. portions of toluene. the toluene extract was washed neutral with aqueous sodium bicarbonate and water, dried over magnesium sulfate, and filtered. Following the removal of the toluene on a rotary evaporator, the residue was vacuum distilled and the diethyl nitromalonate boiling at 97°–99° at 1.7 mm. Hg was collected.

A solution of 1.2 g. sodium in 75 ml. of absolute ethanol was slowly added with agitation to 10.3 g. of the above diethyl nitromalonate in 75 ml. of absolute ethanol at 0°C. To this solution was slowly added 8.0 g. $Br_2$ with agitation followed by the addition of 200 ml. of a saturated aqueous solution of sodium chloride. The aqueous mixture was extracted three times with 200 ml. portions of ether, the combined ether extracts dried over magnesium sulfate, and then filtered. The ether was removed on a rotary evaporator and the residue distilled, collecting the diethyl bromonitromalonate (I) boiling at 143°–145°C at 15 mm. Hg.

In a similar manner, starting with the corresponding malonic acid ester, were prepared:

Dimethyl bromonitromalonate (II), b.p. 128°–129°C at 10 mm. Hg.

Di-n-butyl bromonitromalonate (III), b.p. 120°C at 0.1 mm. Hg.

Di-n-propyl bromonitromalonate (IV), b.p. 82.5°C at 0.01 mm. Hg.

EXAMPLE II

The following tests demonstrate the effectiveness of our compounds as preservatives for cutting oil emulsions. A 6% solution, by weight, of the compounds were prepared and serially diluted in ethanol to give a range of concentrations. Two cutting oil emulsions were prepared; the first was made by diluting one part of Kutwell 30 cutting oil with 100 parts of distilled water and the second by diluting one part of Kutwell 30 with 30 parts of distilled water. Kutwell 30 (manufactured by Humble Oil and Refining Co.) is an emulsifiable sulfonated lubricant cooling solution used in the turning, cutting and grinding of metals. Peptone (Difco) was added to give a 0.1% concentration in each emulsion and the emulsions were sterilized. Aliquots (0.1 ml.) of the serial dilution series were then added to 12 ml. of the cooled cutting oil emulsions. The samples were inoculated with one drop (0.05 ml.) of a 24 hour nutrient broth culture of *Pseudomonas aeruginosa* and incubated at 28°C on a gyratory shaker for a 4-week period. The presence of viable organisms was determined at weekly intervals and the emulsions reinoculated. Thus, each preparation had been inoculated four times by the beginning of the fourth week. Viable organisms were detected by streaking one 4 mm. loopful (0.01 ml.) of emulsion onto the surface of trypticase glucose extract agar (Baltimore Biological Laboratories, Baltimore, Maryland) containing 0.005% triphenyl tetrazolium chloride and letheen antidote.

TABLE I

The minimum concentration of compound required for complete inhibition of *Ps. aeruginosa* in emulsion ($\mu g/ml.$) is presented in the table below.

| Compound No. | Week 1 | | Week 2 | | Week 3 | | Week 4 | |
|---|---|---|---|---|---|---|---|---|
| | 1:100 | 1:30 | 1:100 | 1:30 | 1:100 | 1:30 | 1:100 | 1:30 |
| I | 15.6 | 15.6 | 15.6 | 15.6 | 31.25 | 31.25 | 31.25 | 31.25 |

-continued

| Compound No. | Week 1 | | Week 2 | | Week 3 | | Week 4 | |
|---|---|---|---|---|---|---|---|---|
| | 1:100 | 1:30 | 1:100 | 1:30 | 1:100 | 1:30 | 1:100 | 1:30 |
| II | 15.6 | 15.6 | 15.6 | 15.6 | 15.6 | 15.6 | 15.6 | 15.6 |
| III | 250 | >500 | 250 | 500 | 250 | 500 | 250 | 500 |
| IV | 125 | 250 | 125 | 250 | 125 | 250 | 125 | 250 | concentration through the 4 week incubation period were as follows:

| | Minimum Inhibitory Concentration (mcg/ml.) | | | | | | | |
|---|---|---|---|---|---|---|---|---|
| | Formula A | | Formula B | | Formula C | | Formula D | |
| Compound No. | Ps.a. | A.n. | Ps.a. | A.n. | Ps.a. | A.n. | Ps.a. | A.n. |
| I | <30 | <30 | 60 | 500 | <30 | <30 | <30 | <30 |
| II | <30 | <30 | <30 | <30 | <30 | <30 | <30 | <30 |

EXAMPLE III

The effectiveness of our compounds in cosmetic compositions was demonstrated by the following tests. Serial dilutions of the compounds in dimethylformamide were added to prepared, sterile, cosmetic lotions of the following compositions:

| Formula A | (Parts by Weight) |
|---|---|
| Stearic acid | 1.4 |
| Mineral oil | 2.3 |
| Arlacel 60 (sorbitan monostearate) | 0.7 |
| Tween 60 (polyoxyethylene sorbitan monostearate) | 1.6 |
| Water | 94.0 |

| Formula B | (parts by weight) |
|---|---|
| Tetrahydrosqualene | 5.2 |
| Alcolec 4135 | 1.6 |
| Polyethyleneglycol 400 monostearate | 2.1 |
| Cetyl Alcohol | 1.1 |
| Water | 90.0 |

| Formula C | (parts by weight) |
|---|---|
| Stearic acid | 3.0 |
| Tween 60 | 2.9 |
| Amerchol L-101 | 6.0 |
| Modulan | 2.0 |
| Span 60 | 2.1 |
| Water | 84.0 |

| Formula D | (parts by weight) |
|---|---|
| Mineral oil | 30.0 |
| Cetyl alcohol | 1.0 |
| Amerchol L-101 | 5.0 |
| Arlacel 165 | 4.0 |
| Solulan 98 | 2.0 |
| Glycerol | 4.0 |
| Water | 54.0 |

The finished formulations were fortified with a 0.1% each, peptone (Difco), yeast extract (Difco), and malt extract (Difco), nutrients that insure the rapid development of the test organisms. Each of the products, containing varying levels of the compounds were divided in two and one inoculated with a spore suspension of A.niger, the other with a 24 hour nutrient broth culture of Ps.aeruginosa. These organisms are frequently found as contaminants in cosmetic products. The samples were incubated for a 4 week period with weekly examinations for the growth of the organisms. At weekly intervals the samples were also reinoculated with the test organisms. Presence of fungal growth was determined macroscopically while bacterial contamination was determined by the method described in Example II. Results of these tests showing the minimum inhibitory

EXAMPLE IV

To demonstrate the activity of compounds of this invention is a simulated white water system, a slimicide test suggested in "Microbiology of Pulp and Paper, TAPPI Monograph Series, No. 15", was used. The compounds were dissolved in dimethylformamide and constant volumes of suitable dilution levels were added to flasks containing 24 ml. of the following substrate:

8.4 g. Whatman No. 2 powdered cellulose
2.6 g. Sodium nitrate
1.0 g. Calcium sulfate
6.5 g. Maltose
1.0 g. Nutrient Broth, Difco
10.0 ml. 2% Mersize RM 70R (Monsanto)
2.5 ml. 2% Alum
900 ml. distilled water Using pure culture technique, the flasks were inoculated with 1 drop of an 18–24 hour Nutrient Broth culture of bacteria and an aqueous conidia suspension of fungi grown on Potato Dextrose Agar. The flasks were agitated continuously on a gyratory shaker at 28°C. The presence of bacterial growth was determined after 7-day incubation by streaking onto Dextrose Tryptone Extract Agar plates with Letheen. Fungal growth was detected visually after 7 days incubation. Control flasks included in these tests showed heavy growth of the organisms during this incubation period. The results listed below are the minimum concentration of the compound that completely inhibited growth.

| Organism | Inhibitory Conc. (mcg./ml.) | | | |
|---|---|---|---|---|
| | I | II | III | IV |
| Ps. aeruginosa | 62 | 31 | 250 | 125 |
| A. aerogenes | 62 | 31 | 125 | 62 |
| A. niger | 62 | 31 | 125 | 125 |
| P. piscarium | 62 | 31 | 125 | 125 |

The compounds of our invention may be incorporated into these systems directly or dissolved in various organic solvents, alone or formulated with other biocides and/or additives used in paper mill systems.

EXAMPLE V

The compounds of our invention effectively inhibit the growth of microorganisms in cooling water as shown by the following tests. A sample of cooling tower water was taken from an installation which had been in operation in a chemical plant for several years. The installation consisted of a two-cell induced draft double flow tower and accessory equipment designed to cool 2,400 gallons per minute from 95°F to 85°F. It was composed of redwood structural members with plastic fill and had a capacity of about 10,000 gallons. The water sample was divided into several 150 ml. aliquots and dimethylformamide solutions of the compounds added to give various concentrations by weight of the water. Dimethylformamide alone was added to one of the samples and served as a control. The total aerobic bacterial count of the samples was determined immediately and after 24 hours incubation on a gyratory shaker by standard plating methods, results are listed in the table below:

| Conc./ | Counts per milliliter | | | |
|---|---|---|---|---|
| | Compound I | | Compound II | |
| mcg/ml.) | 0 hrs. | 24 hrs. | 0 hrs. | 24 hrs. |
| 0 | $53 \times 10^4$ | $143 \times 10^4$ | $53 \times 10^4$ | $143 \times 10^4$ |
| 25 | $79 \times 10^4$ | 0 | $52 \times 10^4$ | 0 |
| 50 | $52 \times 10^4$ | 0 | $101 \times 10^4$ | 0 |

EXAMPLE VI

The activity of our compounds was tested against *D. desulfuricans* under anaerobic conditions using Difco Sulfate API broth. The compounds were added to the media as dilutions of solutions in dimethylformamide and the media was incubated at 27°C for 30 days. At the end of the period the media was visually examined for microbial growth. The activity of the compounds tabulated below attests to their usefulness as biocides in this application. The chemical can be added to flood water systems formulated in the various aliphatic and aromatic solvents perviously described in this application.

| Chemical | Minimum Inhibitory Concentration (mcg/ml.) |
|---|---|
| I | 50 |
| II | 50 |
| III | 100 |
| IV | 50 |

EXAMPLE VII

The compounds of our invention are effective preservatives for emulsion paints as demonstrated by the following tests. The test paint was an acrylic emulsion interior paint, containing no preservatives. The paint composition was as follows:

| Water | 20.7 g. |
|---|---|
| Daxad 30 | 0.8 |
| Triton X-100 | 0.2 |
| Clearate WD | 10.4 |
| Ti-Pure R-901 | 25.0 |
| Lorite | 30.0 |
| Duramite | 10.0 |
| Wallastone P4 | 5.0 |
| 2% QP 15000 Sol. | 12.7 |
| Ethylene Glycol | 2.0 |
| Everflex BG | 27.0 |
| Texanol | 1.8 |

Various concentration levels of the compounds in ethanol were added to the paint, and these samples were inoculated with a microbially spoiled paint containing large numbers of actively growing *Pseudomonas aeruginosa*. The survival of the bacteria in the samples was determined by swab streaking the paints onto dextrose trypticase extract agar, initially and after 24 hours, 1, 2, and 4 weeks incubation at ambient temperatures. Results are listed in the table below.

| Compound No. | Minimum Inhibitory Concentration (mcg/ml. | | | |
|---|---|---|---|---|
| | 24 hrs. | 1 week | 2 weeks | 4 weeks |
| I | <62.5 | <62.5 | <62.5 | <62.5 |
| II | <62.5 | <62.5 | <62.5 | 62.5–125 |

EXAMPLE VIII

The utility of our compounds as biocides in rolling mill oils and emulsions was demonstrated by the following tests. A rolling mill emulsion was prepared by diluting a commercially available emulsified rolling mill concentrate, Prisol 44 (Mobile Oil Co.) 1 to 20 with water. The emulsion was fortified with 0.1% peptone and small quantities of aluminum and steel shavings added to simulate use conditions. Various concentrations of our compounds were added to the emulsions as aliquots of ethanol solutions and the samples inoculated with a mixture of gram negative microorganisms of a contaminated emulsion obtained from a rolling mill plant. The samples were incubated on a rotary shaker, examined weekly for the presence of microorganisms as previously described, and then reinoculated. Results of these tests after a 4 week incubation period were as follows:

| Compound No. | Minimum Inhibitory Concentration (mcg/ml.) |
|---|---|
| I | 62.5 |
| II | <31 |

EXAMPLE IX

The effectiveness of our compounds in preventing microbial growth in "spin finishes" was shown in tests on Nopco 1296 (Nopco Chemical Co.), a textile lubricant concentrate. This lubricant was diluted 1 to 4 with water and various concentrations of our compounds were added as solutions in ethanol. These emulsions were inoculated with a nutrient broth culture of microorganisms from a contaminated "spin finish" obtained from a textile plant. The samples were incubated on a gyratory shaker, examined weekly for microbial growth, and then reinoculated. Results of these tests after a 4 week period were as follows:

| Compound No. | Minimum Inhibitory Concentration (mcg/ml.) |
|---|---|
| I | 125 |
| II | <31 |

EXAMPLE X

The utility of our compounds in protecting polymer emulsions from microbial deterioration was shown by the following tests in an acrylic emulsion. Varying levels of the compounds were added as ethanol solutions to samples of "Rhoplex B-15" acrylic emulsion (Rohm and Haas Co.). The samples were inoculated with a viable broth culture of *Pseudomonas aeruginosa* and incubated in closed container at 28°C for a 4 week period. The presence of surviving bacteria were determined at weekly intervals using plating techniques described in previous examples and the samples were reinoculated weekly. Results of these tests showing the minimum concentration of the compounds required to prevent survival of the bacteria throughout the test period are listed below.

| Compound No. | Minimum Effective Concentration (mcg/ml.) |
| --- | --- |
| I | 62.5 |
| II | 31.3 |

EXAMPLE XI

Deterioration of adhesives, particularly starch base adhesives, not containing preservatives is commonly encountered in practice. Efficacy as a starch base adhesive was demonstrated by inoculation of a 6% solution of corn starch, partially hydrolyzed by holding at 100°C. for 5 minutes. In order to insure good growth of the test organisms, the starch base was fortified with nutrients to contain 0.1% each of Malt Extract (Difco) and Peptone (Difco).

Various concentrations of the compounds were added to the adhesive as serial dilutions of a dimethylformamide solution. Replicate samples were prepared for each concentration level and inoculated by pure culture technique with *Pseudomonas aeruginosa*, *Aspergillus niger*, and *Pencillium piscarium*. The samples were incubated at 28°C for a 4 week period and examined for microbial growth. Presence of *Ps. aeruginosa* was determined by previously described plating techniques and *A. niger* and *P. piscarium* growth was detected macroscopically. Results of these tests are recorded below.

| Compound No. | Conc. (mcg/ml.) | 4 Week Incubation | | |
| --- | --- | --- | --- | --- |
| | | Ps.aeruginosa | A.niger | P.piscarium |
| I | 250 | − | − | − |
| I | 125 | − | − | − |
| I | 62.5 | − | − | − |
| I | 31.3 | + | + | − |
| I | 15.6 | + | + | + |
| II | 250 | − | − | − |
| II | 125 | − | − | − |
| II | 62.5 | − | − | − |
| II | 31.3 | − | + | − |
| II | 15.6 | + | + | − |

− = No growth
+ = Growth

We claim:

1. A method of preventing or eliminating the growth of bacteria and fungi in an aqueous composition subject to spoilage thereby, which comprises incorporating in said composition an effective amount of a compound of the formula

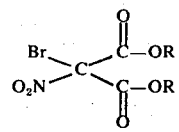

where in R is a straight chain alkyl group having from 1 to 4 carbon atoms.

2. A method according to claim 1 wherein there is utilized from between 0.0001% to 0.1% by weight of said compound.

3. A method according to claim 2 which comprises adding from about 20 to about 125 mcg of said compound to each 1 ml. of the aqueous system.

4. The method of claim 1 wherein the aqueous composition is process water used in pulp and paper manufacture.

5. The method of claim 1 wherein the aqueous composition is industrial cooling water.

6. The method of claim 1 wherein the aqueous composition is secondary oil recovery flood water.

* * * * *